United States Patent [19]

Koshiishi et al.

[11] Patent Number: 5,138,251

[45] Date of Patent: Aug. 11, 1992

[54] FET SENSOR APPARATUS OF FLOW-CELL ADAPTIVE TYPE AND METHOD OF MANUFACTURING THE SAME

[75] Inventors: Kiyozou Koshiishi, Sagamihara; Etsuo Shinohara, Hachioji, both of Japan

[73] Assignee: Olympus Optical Co., Ltd., Tokyo, Japan

[21] Appl. No.: 590,467

[22] Filed: Sep. 28, 1990

[30] Foreign Application Priority Data

Oct. 4, 1989 [JP] Japan .................................. 1-259616

[51] Int. Cl.$^5$ .......................................... G01N 27/414
[52] U.S. Cl. .................................. 324/71.5; 324/450; 204/416
[58] Field of Search ............. 324/438, 439, 450, 71.5; 204/416, 418

[56] References Cited

U.S. PATENT DOCUMENTS

| | | | |
|---|---|---|---|
| 4,020,830 | 5/1977 | Johnson et al. | 128/2 E |
| 4,397,714 | 8/1983 | Janata et al. | 204/1 T |
| 4,512,870 | 4/1985 | Kohara et al. | 204/418 X |
| 4,514,263 | 4/1985 | Janata | 204/416 X |
| 4,636,827 | 1/1987 | Rudolf | 324/71.5 X |
| 4,638,346 | 1/1987 | Inami et al. | 324/71.5 X |
| 4,641,084 | 2/1987 | Komatsu | 324/71.5 |
| 4,791,465 | 12/1988 | Sakai et al. | 324/71.5 X |
| 4,961,833 | 10/1990 | Sakai et al. | 204/416 X |

FOREIGN PATENT DOCUMENTS

| | | |
|---|---|---|
| 0063455 | 4/1982 | European Pat. Off. . |
| 0241991 | 10/1987 | European Pat. Off. ........... 324/71.5 |
| 0333861 | 12/1987 | European Pat. Off. . |
| 3727805 | 8/1987 | Fed. Rep. of Germany . |
| 52-26292 | 2/1977 | Japan . |
| 53-25385 | 3/1978 | Japan . |
| 0056746 | 4/1982 | Japan .................................. 324/71.5 |
| 63-9859 | 1/1988 | Japan . |
| 63-11845 | 1/1988 | Japan . |
| 1-83147 | 3/1989 | Japan . |
| 2-167462 | 6/1990 | Japan . |
| 1529743 | 3/1976 | United Kingdom . |
| 2195824 | 8/1987 | United Kingdom . |

OTHER PUBLICATIONS

Walter Heywang-SENSORIK-Dritte, uberarbeitete Auflage Mit 147 Abbildungen, Springer-Verglag, Berlin, Heidelberg, New York, London, Paris, Tokyo—1988.
Research Report, the Committee for Promoting Technical Development, Asahi Glass Kogyo Co., Ltd., vol. 29, 1976, p. 227, FIG. 1(B).
Latest LSI Process Technology p. 314.
Analytical Letters, 20(11), 1765-1772 (1987).

*Primary Examiner*—Kenneth A. Wieder
*Assistant Examiner*—Glenn W. Brown
*Attorney, Agent, or Firm*—Frishauf, Holtz, Goodman & Woodward

[57] ABSTRACT

An FET sensor apparatus comprising a sensor, a base member, and a support. The sensor comprises a semiconductor substrate having a predetermined crystal plane, a field-effect transistor formed on the semiconductor substrate, and a gate portion arranged on at least one of the major surfaces of the semiconductor substrate. The base member has a through hole in which the field-effect transistor is fitted. The support supports the sensor in the through hole in watertight fashion, with said gate portion exposed through an end of the hole.

16 Claims, 7 Drawing Sheets

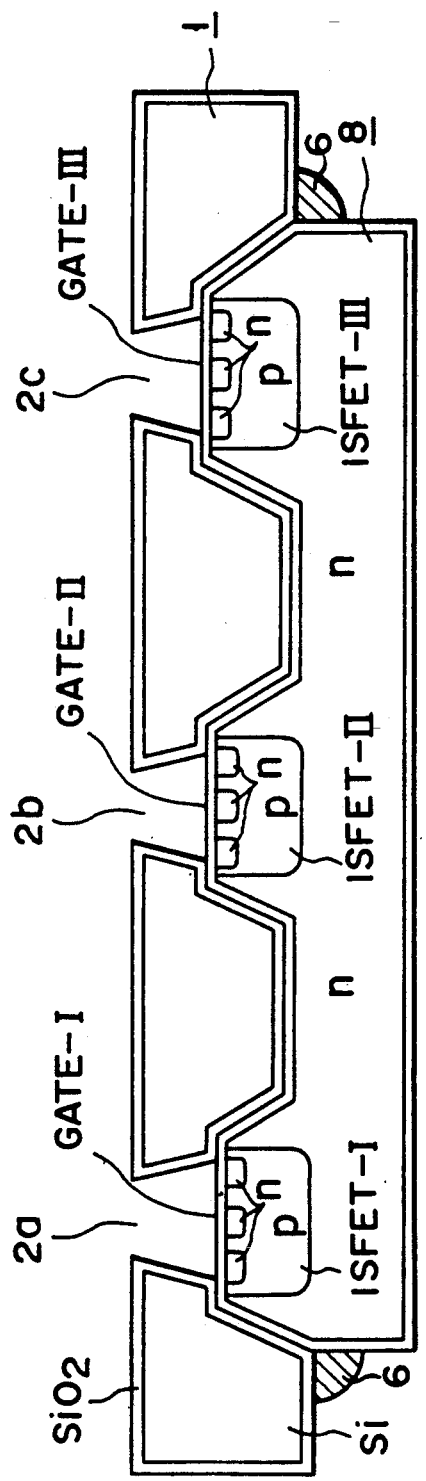
F I G. 5

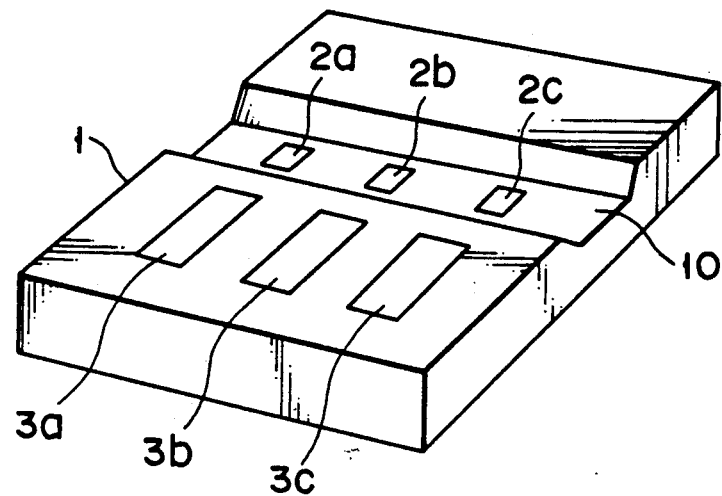
F I G. 6
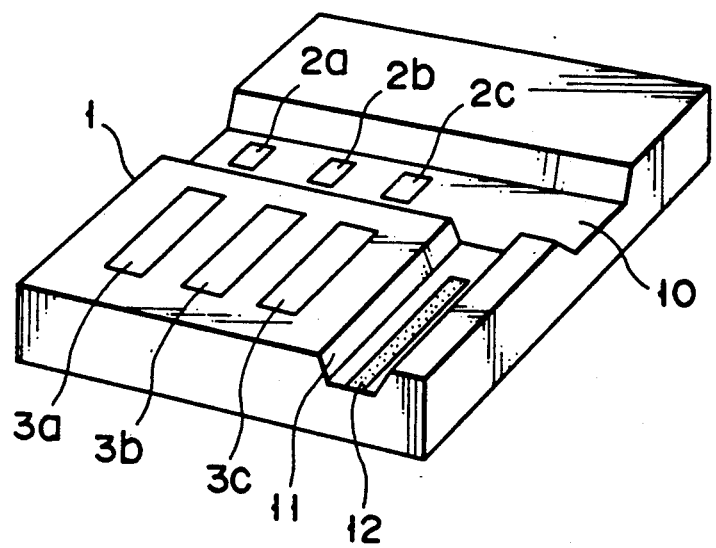
F I G. 7

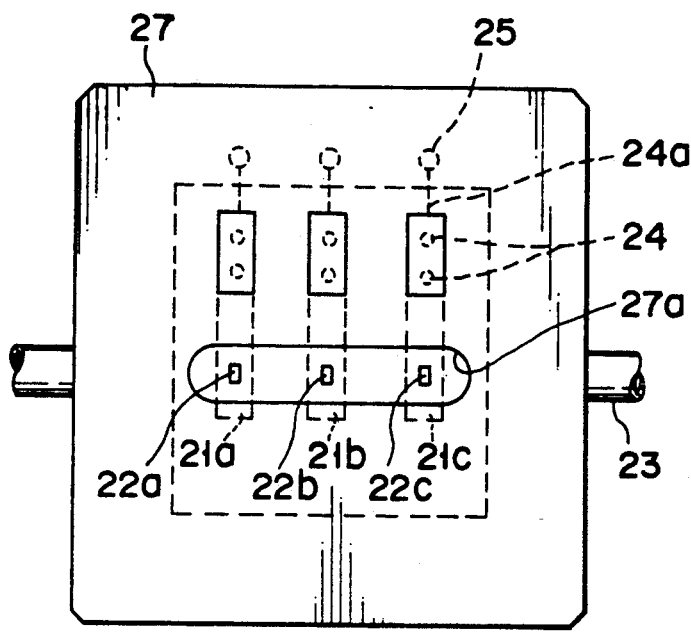
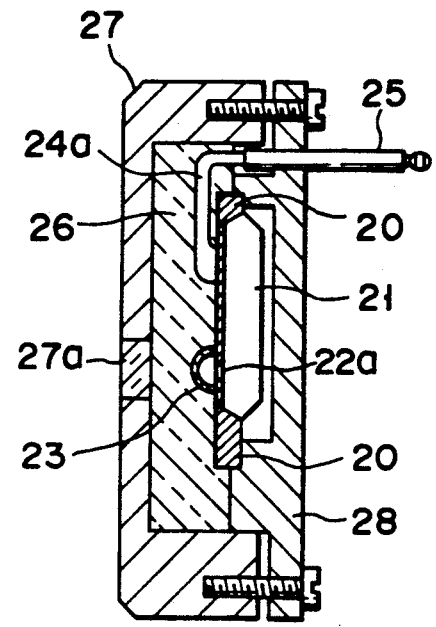
F I G. 8A          F I G. 8B
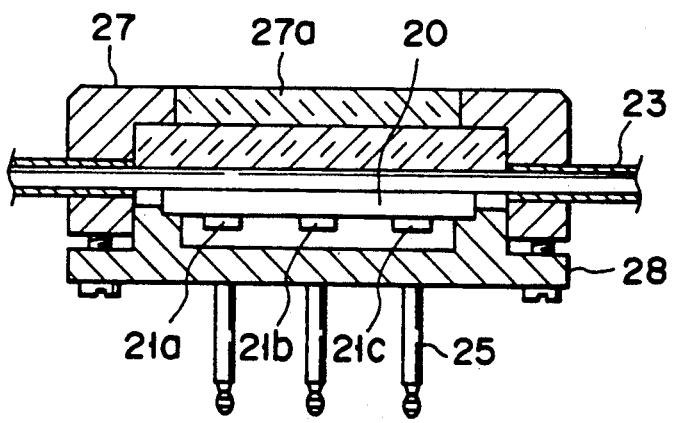
F I G. 8C

FET SENSOR APPARATUS OF FLOW-CELL ADAPTIVE TYPE AND METHOD OF MANUFACTURING THE SAME

BACKGROUND OF THE INVENTION

1. Field of the Invention

The present invention essentially relates to a chemical property sensor apparatus having a field effect transistor (FET) and, more particularly, to an FET sensor apparatus of a flow-cell adaptive type, and also to a method of manufacturing the FET sensor apparatus.

2. Description of the Related Art

Recently, sensors having an FET and designed to perform an electro-chemical analysis on various samples are being developed.

A prototype of such an FET sensor, known as an "ion-sensitive FET (ISFET) sensor," was first proposed by Piet Bergveld in 1972. The principles and operating characteristics of the ISFET sensor have already been determined.

Thereafter, Professor Matsuo at Tohoku University and some other persons invented practical ISFET sensors which have a multi-layered ISFET chiefly made of silicon nitride and which exhibit an improved sensitivity.

Further, U.S. Pat. No. 4,020,830 discloses an FET sensor which has an FET transducer. This FET sensor not only can detect pH degree and inorganic ions, but also can be used in analyzing chemical properties of glucose, urea, enzymes, immune substances, and the like, and can detect gas components such as $O_2$ and $CO_2$.

The FET sensors, thus far proposed and invented, are shaped like a stylus, mostly for two reasons. First, a sensor can easily be applied, if shaped like a stylus, to electro-chemical analysis of living things. Second, it can be manufactured easily if shaped like a stylus.

A stylus-shaped ISFET sensor is disclosed in, for example, Published Unexamined Japanese Patent Application No. 53-25385. This ISFET sensor is manufactured in the following way. First, a comb-shaped unit is made, each tooth of which is an ISFET. Then, the unit is cut into stylus-shaped pieces, i.e., ISFET sensors. This method is practical for mass-production of ISFET sensors.

In use, the stylus-shaped ISFET sensor, thus manufactured, is attached to a catheter, along with a reference electrode, thereby to measure the chemical properties of living tissues. Alternatively, it is immersed in a liquid sample to measure the chemical properties thereof.

To analyze sample blood, for example, a continuous analysis system of flow cell type is employed in most cases. Sensitive elements other than ISFETs, generally known as "ion-sensitive electrodes," are attached to the flow cells of this analysis system. Such an ion sensitive electrode is disclosed in Research Report, the Committee for Promoting Technical Development, Asahi Glass Kogyo Co. Ltd., Vol. 29, 1976, p. 227, FIG. 1(B).

The ion-sensitive elements can be replaced by ISFETs. However, it is very difficult to attach an ISFET to a flow cell since the ISFET is far smaller than an ion-sensitive electrode. Further, there is the risk that the sensitive membrane covering the tip of the ISFET may be broken when the ISFET is attached to the flow cell. Still further, the ISFET, once attached to the flow cell, protrudes therefrom and inevitably disturbs the liquid sample flowing in the flow cell, causing a turbulence in the liquid sample or forming bubbles in the liquid sample. As is known in the art, a turbulence or bubbles in a liquid sample results in incorrect measuring of the chemical properties of the liquid sample. In view of this, a full use cannot be made of an ISFET, though far smaller than an ion-sensitive electrode, when the ISFET is attached to a flow cell.

SUMMARY OF THE INVENTION

It is, therefore, an object of the present invention to provide a new and improved FET sensor apparatus of flow-cell adaptive type, in which ISFETs can be attached to flow cells easily and firmly, which is durable and makes a good use of the excellent characteristics of the ISFETs, achieving micro-measuring with high accuracy.

It is another object of the invention to provide a method of easily manufacturing an FET sensor apparatus of flow-cell adaptive type.

According to one aspect of this invention, there is provided an FET sensor apparatus of a flow-cell adaptive type, comprising:

a sensor comprising a field-effect transistor formed on a semiconductor substrate, the semiconductor substrate having two major surfaces and a predetermined crystal plane, and the field effect-transistor having at least a gate portion arranged on one of the major surfaces of the semiconductor substrate;

a base member having a through hole in which the sensor is fitted; and support means for supporting the sensor in the through hole in watertight fashion, with the gate portion exposed through an end of the through hole.

According to another aspect of the present invention, there is provided a method of manufacturing an FET sensor apparatus of the flow-cell adaptive type, the method comprising the steps of:

etching one major surface of a semiconductor substrate in a semiconductor-manufacturing process, thereby forming a bottomed hole in the major surface, which has predetermined diameter and a predetermined depth;

etching the semiconductor substrate, thereby forming a through hole in the bottom of the bottomed hole, which has a diameter less than that of the bottomed hole, thus forming a gate window; and inserting a sensor into, and fixing the same in, the gate window of the semiconductor substrate, said sensor comprising a semiconductor substrate having two major surfaces and a predetermined crystal plane, a field-effect transistor formed on a semiconductor substrate having the same crystal plane as the semiconductor substrate.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, show the presently preferred embodiments of the invention and, together with the general description give above and the detailed description of the preferred embodiments given below, serve to explain the principles of the invention.

FIG. 5 is a sectional view illustrating a second embodiment of the present invention, which is an FET sensor apparatus comprising a flow-cell substrate and a plurality of comb-shaped ISFETs embedded in the flow-cell substrate;

FIG. 6 is a perspective view of an FET sensor apparatus according a third embodiment of the present invention;

FIG. 7 is a perspective view of a modification of the FET sensor apparatus illustrated in FIG. 6;

FIGS. 8A, 8B, and 8C are a plan view and two sectional views, respectively, showing a flow cell having an FET sensor apparatus which is a fourth embodiment of the present invention.

DETAILED DESCRIPTION OF THE PREFERRED EMBODIMENT

Figure 1A:
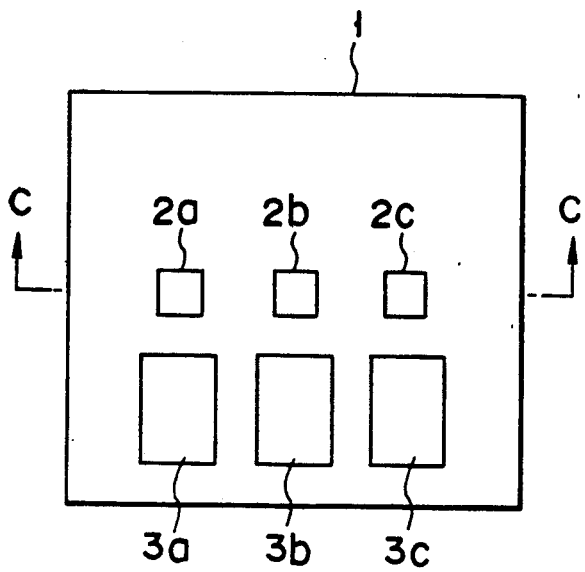
FIGS. 1A to 1C are diagrams showing the flow-cell substrate used in a first embodiment of the invention, FIG. 1A being an upper plan view of the substrate, FIG. 1B being a lower plan view thereof, and FIG. 1C being a sectional view, taken along line C—C in FIG. 1A.

Reference will now be made in detail to the presently preferred embodiments of the invention as illustrated in the accompanying drawings, in which like reference characters designate like or corresponding parts throughout the several drawings.

A first embodiment of the present invention will now be described, with reference to FIGS. 1A-1C, FIGS. 2A and 2B, FIGS. 3A to 3G, and FIGS. 4A to 4C.

Figure 1B:
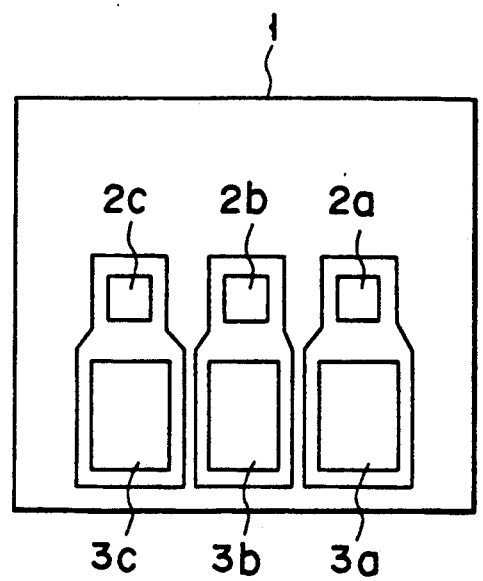
Figure 1C:
Figure 2A:
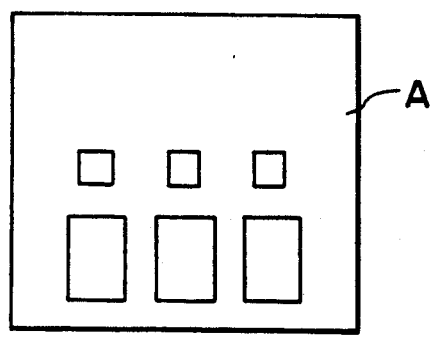
FIGS. 2A and 2B illustrate two etching masks, respectively, used in manufacturing the flow-cell substrate shown in FIGS. 1A to 1C.
Figure 2B:
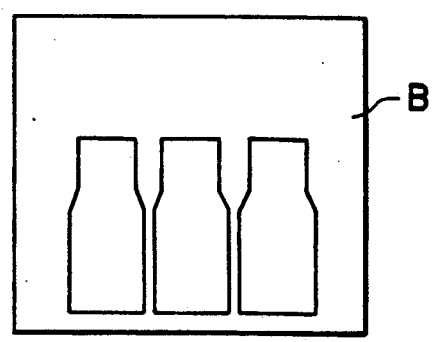

FIGS. 1A to 1C illustrate the flow-cell substrate 1 used in the first embodiment. FIG. 2A is an upper plan view and FIG. 2B is a lower plan view. As FIGS. 1A to 1C clearly show, the flow-cell substrate 1 has three gate windows 2a, 2b, and 2c, and three electrode windows 3a, 3b, and 3c. The substrate 1 is a single-crystal silicon wafer having the same crystal plane as the semiconductor substrate which is used a base member supporting ISFETs as will be described later.

The steps of manufacturing the flow-cell substrate 1 will now be explained, referring to the forming of only one of the windows 2a-2c and 3a-3c.

(1) Forming of Masks

Two etching masks A and B of the types shown in FIGS. 2A and 2B are prepared. Either mask has openings the number of which is determined by the number of the ISFETs to be formed in the flow-cell substrate 1.

(2) Wafer Washing, and Resist Coating

Figure 3A:
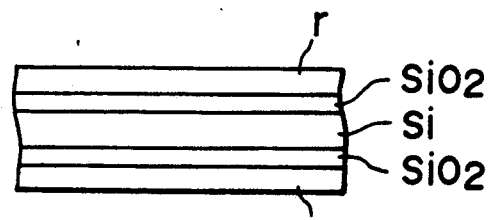
FIGS. 3A to 3G are sectional views, explaining the steps of manufacturing the flow-cell substrate shown in FIGS. 1A to 1C.

First an Si wafer is washed. Then, both major surfaces of the Si wafer are wet-oxidized, thus forming a SiO$_2$ layer on each major surface of the wafer, as is illustrated in FIG. 3A. Further, a resist r is coated on the upper SiO$_2$ layer. Next, this resist r is baked at 140° C. for 30 minutes. A resist r is coated also on the lower SiO$_2$ layer. The resist r, thus coated, is baked at 80° C. for 20 minutes.

(3) Exposure and Developing

Figure 3B:
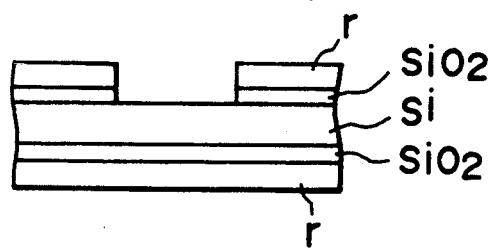
Figure 3C:
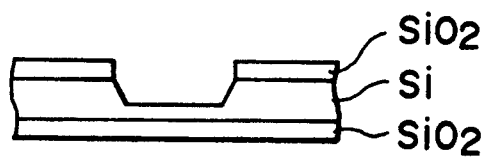

The mask B shown in FIG. 2B is placed on the upper surface of the Si wafer, and the lower surface of the wafer is exposed to light. Then, selected portions of the resist r and the SiO2 layer are etched away, as is shown in FIG. 3B. Next, the remaining portions of the upper resist r are removed from the Si wafer, as is illustrated in FIG. 3C. Further, the lower resist r is also removed, as is shown in FIG. 3C, too.

(4) Si Etching

That portion of the Si wafer, which is exposed through the opening of the upper SiO2 layer, is etched with EPW (Ethylenediamine-Pyrocatechol-Water) at the rate of 2 $\mu$m/min, whereby a recess having sides inclined at about 550° C. is formed in the Si wafer having a crystal face (100) plane, as is illustrated in FIG. 3C. (The EPW etchant is disclosed in Published Unexamined Japanese Patent Application No. 53-25385.) Thereafter, the upper SiO$_2$ layer is removed from the Si wafer.

(5) Exposure and Developing

Figure 3D:
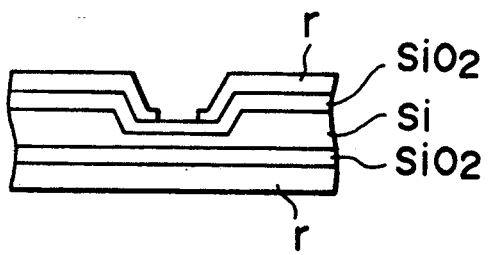

After removing the upper SiO$_2$ layer, the Si wafer is washed with RCA and wet-oxidized for the second time, thus forming an SiO$_2$ layer on the upper surface of the Si wafer as is illustrated in FIG. 3D. Next, a resist r is coated on the upper SiO$_2$ layer. This resist r is baked at 140° C. for 30 minutes. Then, a resist r is coated on the lower SiO$_2$ layer, and is baked at 80° C. for 5 minutes. Further, another resist is coated on the resist r coated on the lower SiO$_2$ layer and subsequently baked at 80° C. for 20 minutes. Next, the mask A shown in FIG. 2A is placed on the resist r formed on the upper SiO$_2$ layer. Light is applied to this resist r, thereby forming an opening in the resist r as is shown in FIG. 3D.

(6) Etching of SiO$_2$

Figure 3E:
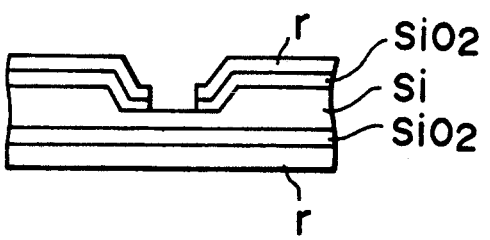

After the entire structure shown in FIG. 3D has been post-baked, the upper SiO$_2$ layer is etched, thus forming an opening in this SiO$_2$ layer, as is illustrated in FIG. 3E.

(7) Etching of Si

Figure 3F:
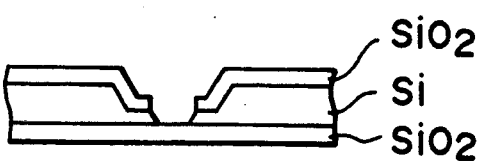

After the upper SiO$_2$ layer has been thus etched, both resists r are removed, and the Si wafer is etched with EPW at the same rate of 2 $\mu$m/min as in the first Si-etching step (4). As a result of this, the structure shown in FIG. 3F is obtained.

(8) Finishing

Figure 3G:

Then, both the upper SiO$_2$ layer and the lower SiO$_2$ layer are removed, and the Si wafer is washed with RCA. The Si wafer, thus washed, is wet-oxidized, thus forming an SiO$_2$ layer which covers all surfaces of the Si wafer as is illustrated in FIG. 3G.

The Si wafer, which has crystal face (100) plane, can be replaced by a Si wafer having a crystal face (110) plane.

As is shown in FIG. 1C, the flow-cell substrate 1, thus made, has through holes 2a-2c and 3a-3c, each consisting of a large portion and a small portion. The large portion opens at the lower surface, and the small portion opens at the upper surface. Either portion of each through hole diverges downward at an angle of about 55°.

Figure 4A:
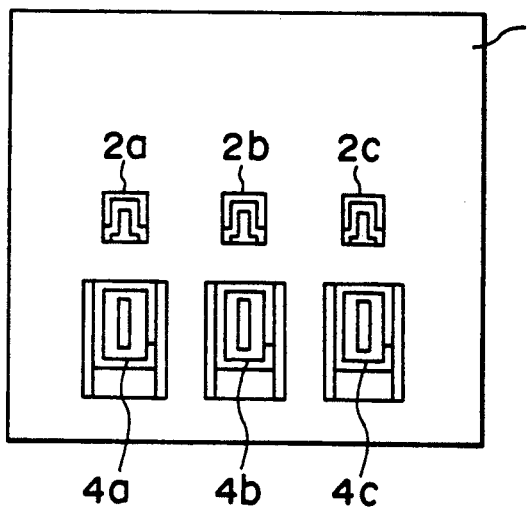
FIGS. 4A to 4C are diagrams explaining the steps of inserting ISFETs into the through holes of the flow-cell substrate illustrated in FIGS. 1A to 1C.
Figure 4B:
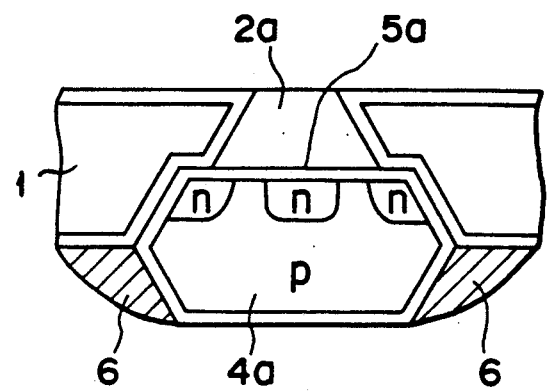
Figure 4C:
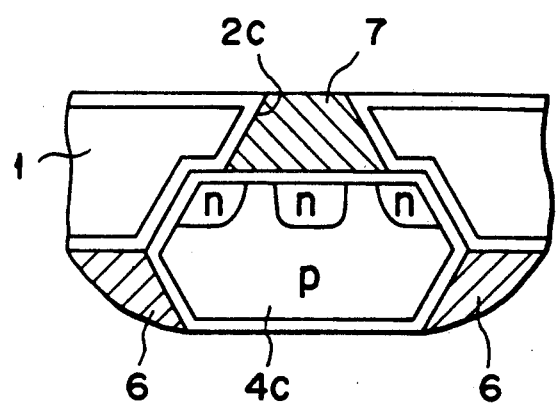

Three ISFETs 4a, 4b, and 4c manufactured by the known method, each shaped like a stylus i.e., hexagonal having two elongate opposed sides and having the structure shown in FIG. 4B, are inserted into the large portions of the through holes 2a-2c and 3a-3c of the flow-cell substrate 1. As is shown in FIG. 4A, the gate portions 5a-5c of the ISFETs 4a-4c are seen through the gate windows 2a-2c, respectively. Adhesive 6 such as an epoxy resin is applied into the gap between each ISFET and the large portion of the windows. Each gate window, e.g., the window 2a, can be either left unfilled as is shown in FIG. 4B or filled with sensitive membrane 7 as is shown in FIG. 4C. When the window 2a is left unfilled, the ISFET 4a is covered by an $Si_3N_4$ membrane and can thus be used to measure the pH degree of a liquid sample. On the other hand, when the window 2a is filled with the sensitive membrane 7, the ISFET 4a can be used to measure $Na^+$ ions, $K^+$ ions, or the like, depending on the nature of the sensitive membrane 7. The membrane 7 can easily be prepared by mixing a sensitive material with, for example, a solution made by dissolving polyvinyl chloride (PVC) in tetrahydrofuran (THF).

The flow-cell substrate 1 and the ISFETs are made of single-crystal silicon and have the same crystal plane. Thus, the substrate 1 and the ISFETs can be made by the same semiconductor-manufacturing process, and the ISFETs can be fitted tightly in the craters (i.e., the recesses) of the substrate 1 which have been formed by etching. As a result of this, the ISFETs can be set at correct positions. Moreover, the ISFETs are well insulated electrically from the Si substrate 1 since a $SiO_2$ film covers all surfaces of the flow-cell substrate 1. In addition, the $SiO_2$ film covering the Si substrate 1 is so smooth that the ISFETs can firmly contact the bottoms of the craters of the substrate 1.

The FET sensor apparatus, described above and best shown in FIG. 4A, has three ISFETs. Nevertheless, more or less than three ISFETs can of course be used according to the present invention. Further, the holes 2a to 2c of the flow-cell substrate 1 consist each of two portions, i.e., a large portion and a small portion. Instead, each hole can be one having tapered surfaces.

FIG. 5 is a sectional view showing a second embodiment of the present invention. This embodiment is an FET sensor apparatus comprising a flow-cell substrate 1 and an ISFET assembly 8 shaped like a comb and partly fitted in the holes 2a, 2b and 2c made in substrate 1. The ISFET assembly 8 comprised three ISFETs I, II, and III, which are perfectly insulated electrically from one another, though physically connected to one another. More precisely, the ISFETs I, II, and III are formed in the same substrate, constituting the assembly 8, and are spaced apart at such intervals that they are fitted in the holes 2a, 2b and 2c of the flow-cell substrate 1, respectively. As is evident from FIG. 5, the pn junctions of the ISFETs are isolated from one another.

This pn-junction isolated structure is formed by diffusing boron into a n-type substrate, and three p-type regions are formed in the n-type substrate. These p-type regions make the ISFET elements. Phosphorus is diffused into each p-type region, thereby forming a source and a drain therein, whereby an ISFET is formed. When a reverse bias is applied to the pn junction of the ISFET thus formed, the ISFET is electrically isolated from the other ISFETs.

The FET sensor apparatus shown in FIG. 5 can be manufactured more easily than the apparatus of the first embodiment, since it has the ISFET assembly 8 comprising the ISFETs I, II, and III electrically isolated but physically connected to one another, whereas the first embodiment has physically separated ISFETs 4a, 4b, and 4c as is shown in FIG. 4A.

The ISFETs I, II, and III can be isolated by any method other than forming pn-junctions. Air isolation, insulative isolation, or complete isolation can be employed. These methods of isolation of ISFETs are described in detail in Latest LSI Process Technology, p. 314.

FIG. 6 is a perspective view of an FET sensor apparatus according a third embodiment of this invention. This apparatus is characterized in that its flow-cell substrate 1 has a groove 10 for a passage of liquid sample. The groove 10 can be easily formed by the known semiconductor-manufacturing process such as anisotropic etching.

FIG. 7 is a perspective view showing a modification of the FET sensor apparatus illustrated in FIG. 6. This apparatus also has a groove 10 for guiding a liquid sample. Further, it has another groove 11 connected to the groove 10 and a thin reference electrode 12 made of Ag or AgCl and formed on the bottom of the groove 11. The groove 11 can be formed by the known semiconductor-manufacturing process, and the reference electrode 12 can be formed by the known method employed in manufacturing semiconductor devices.

The groove 11 can take a different position. For example, it can be connected to the left end of the groove 10, not to the right end thereof as is shown in FIG. 6. The reference electrode 12 can be replaced by a reference ISFET in which case the groove 11 need not be formed in the surface of the flow-cell substrate 1 since the reference ISFET can be positioned in the same manner as the other ISFETs. An ISFET which can be used as the reference ISFET is disclosed in Anal. Letters, Vol. 20, 1987, pp. 1765–1772.

FIGS. 8A, 8B, and 8C illustrate a flow cell having an FET sensor apparatus which is a fourth embodiment of the present invention. The flow cell is designed to measure the chemical properties of liquid samples, such as blood samples, continuously one after another. As is shown in FIGS. 8A, 8B, and 8C, the flow cell comprises a flow-cell substrate 20 and three ISFETs 21a, 21b and 21c formed in the surface of the substrate 20. The flow cell has a liquid passage 23 which allows a liquid sample to flow through gate windows 22a, 22b, and 22c of the ISFETs 21a, 21b, and 21c, and hence contact the ISFETs 21a, 21b, and 21c, respectively. More specifically, the passage 23 is a horizontally extending tube having an elongate opening in the middle portion. This elongated opening, made by cutting away the upper half of the middle portion, faces the gate openings 22a to 22c of the ISFETs 21a to 21c. Lead wires 24a connect the terminals 24 of the ISFETs 21a to 21c to three electrode pins 25.

The flow-cell substrate 20, the ISFETs 21a to 21c, the liquid passage 23, the lead wires 24a, and the electrode pins 25 are fastened together by transparent mold resin 26, thus constituting a unit. This unit is placed within a decorative case 27, and a cover 28 is fastened to the case 27, closing the opening of the case 27. The flow cell is thereby assembled.

That portion of the case 27, which is located above the gate windows 22a to 22c, is a transparent view window 27a. It is through this window 27a that the liquid sample flowing through the liquid passage 23 can be seen from outside.

In the flow cell described above, the liquid sample can directly contact the gates of the ISFETs 21a, 21b, and 21c, while flowing through the liquid passage 23, but cannot contact any other portions of each ISFET. Hence, neither water nor metal ions, which may impair the function of the ISFETs 21a to 21c, penetrates into the ISFETs 21a to 21c. The flow cell can, theretofore, be durable and can accurately measure the chemical properties of liquid samples. Moreover, there is no risk that the sensing ability of the ISFETs 21a to 21c decreases since nothing can touch the ISFETs 21a to 21c while the flow cell is being assembled, and nothing but liquid sample can touch them while the flow cell is being used.

Figure 9:
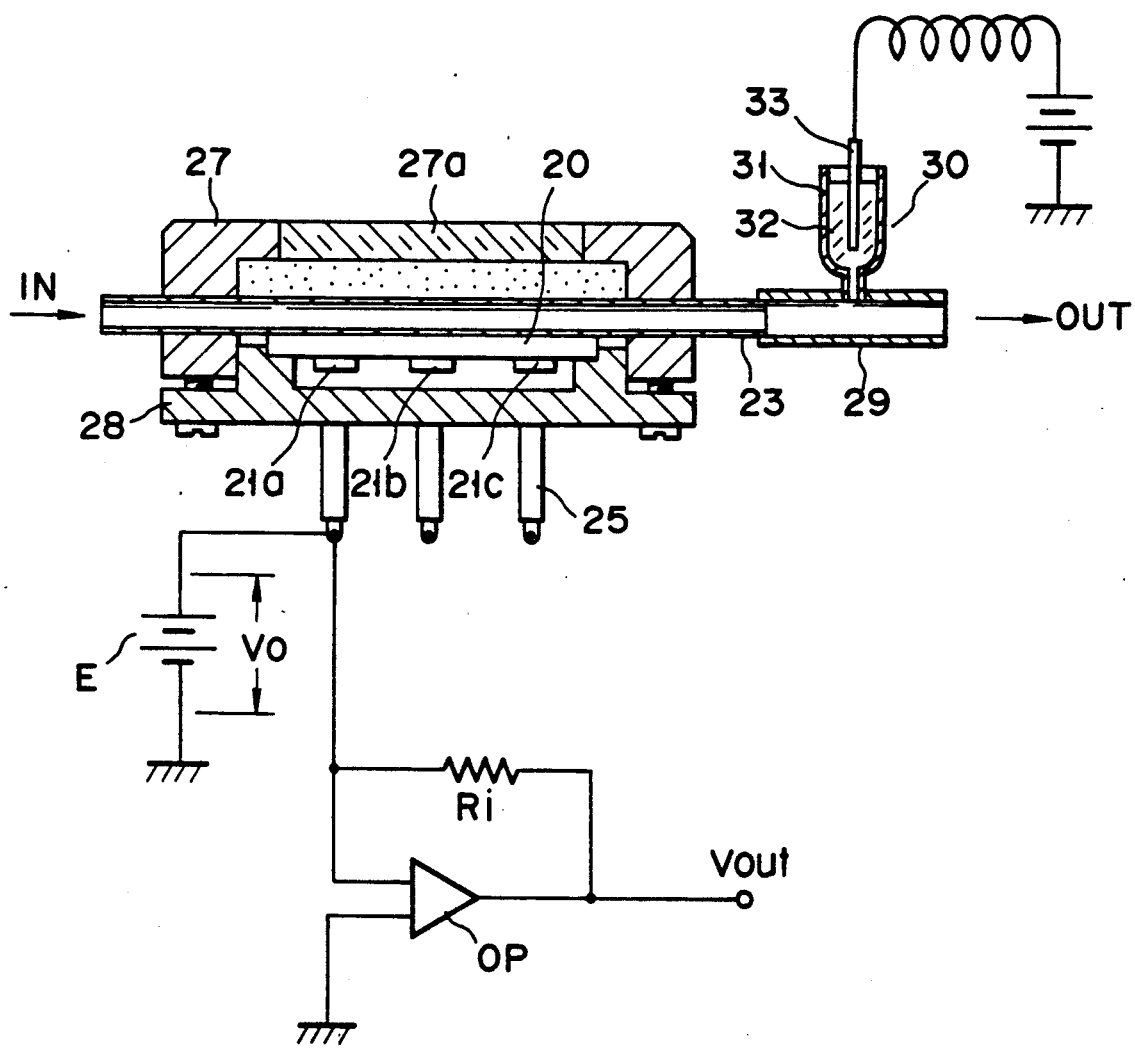
FIG. 9 is a diagram showing the flow cell shown in FIGS. 8A to 8C, and also a reference electrode and a drive circuit both used in combination with the flow cell in order to measure the chemical properties of a liquid sample.

FIG. 9 is a diagram showing a system for analyzing liquid samples, which comprises the flow cell shown in FIGS. 8A to 8C, a tube 29 connected to the outlet end of the liquid passage 23 of the flow cell, a reference electrode 30 connected to the tube 29, a drive circuit E connected to the electrode pins 25 of the flow cell, and an output circuit. The reference electrode 30 comprises a glass tube 31 and Ag or AgCl electrode 33 inserted in the glass tube 31. The tube 31 is filled with a KCl solution 32, and the electrode 33 is, thus immersed in the KCl solution 32.

The drive circuit E shown in FIG. 9 is nothing more than a DC source for applying a voltage V0 to the electrode pin 25 of the first ISFET 21a, and the output circuit shown in FIG. 9, which is connected to the pin 25 of the first ISFET 21a comprises a feedback resistor Ri, and operational amplifier OP, and an output terminal Vout. In practice, however, such a drive-output system as is disclosed in U.S. Pat. No. 4,641,084, to the assignee of the present application, should better be incorporated in the sample-analyzing system illustrated in FIG. 9.

As has been described above, the present invention can provide a new and improved FET sensor apparatus which comprises a semiconductor substrate having a predetermined crystal plane and through holes, and ISFETs fitted in the through holes and made of material having the same crystal plane as the substrate, and which can, therefore, be durable and can perform micromeasuring with high accuracy. Also, the present invention can provide a method of manufacturing this FET sensor apparatus.

Additional embodiments of the present invention will be apparent to those skilled in the art from consideration of the specification and practice of the present invention disclosed herein. It is intended that the specification and examples be considered as exemplary only, with the true scope of the present invention being indicated by the following claims.

What is claimed is:

1. An FET sensor apparatus of flow-cell adaptive type, comprising:
    a sensor comprising a field-effect transistor formed on a semiconductor substrate, the semiconductor substrate having two major surfaces and a predetermined crystal plane, and the field-effect transistor having at least a gate portion arranged on one of the major surfaces of the semiconductor substrate;
    a base member having a through hole in which said sensor is fitted; and
    support means for supporting said sensor in the through hole in watertight fashion, with said gate portion exposed through an end of said through hole;
    wherein said through hole of said base member has a shape complementary to that of said sensor; and
    wherein said through hole of said base member has a tapered surface and said sensor is exposed through the opening of said through hole having a smaller diameter.

2. The FET sensor apparatus according to claim 1, wherein said through hole includes a tapered small-diameter portion and a tapered large-diameter portion, and said sensor is fitted in the large-diameter portion of said through hole.

3. The FET sensor apparatus according to claim 1, further comprising material sensitive to a specific material, said sensitive material filling in the through hole of said base member to cover on the gate portion of said sensor.

4. The FET sensor apparatus according to claim 1, wherein said sensor is hexagonal in shape with two elongate opposed sides.

5. The FET sensor apparatus according to claim 1, wherein said base member has an electrode window aligned with said through hole.

6. An FET sensor apparatus of flow-cell adaptive type, comprising:
    a sensor comprising a field-effect transistor formed on a semiconductor substrate, the semiconductor substrate having two major surfaces and a predetermined crystal plane, and the field-effect transistor having at least a gate portion arranged on one of the major surfaces of the semiconductor substrate;
    a base member having a through hole in which said sensor is fitted; and
    support means for supporting said sensor in the through hole in watertight fashion, with said gate portion exposed through an end of said through hole;
    wherein said base member is made of a semiconductor substrate of the same type as said semiconductor substrate of said sensor;
    the through hole of said base member has a shape complementary to that of said sensor; and
    wherein the through hole of said base member is tapered, and said sensor has a gate portion exposed through the smaller end of the through hole.

7. The FET sensor apparatus according to claim 6, wherein said semiconductor substrate forming said base member has an insulation film which covers least that portion which has said through hole.

8. The FET sensor apparatus according to claim 6, wherein said tapered through hole includes a tapered large-diameter portion and a tapered small-diameter portion, and said sensor is fitted in the tapered large-diameter portion of said through hole.

9. An FET apparatus of flow-cell adaptive type, comprising:
    a sensor comprising a field-effect transistor formed on a semiconductor substrate, the semiconductor substrate having two major surfaces and a predetermined crystal plane, and the field-effect transistor having at least a gate portion arranged on one of the major surfaces of the semiconductor substrate;
    a base member having a through hole in which said sensor is fitted; and
    support means for supporting said sensor in the through hole in watertight fashion, with said gate portion exposed through an end of said through hole;

wherein said base member has a passage for a liquid sample, and said through hole opens to said passage; and wherein said base member has a groove communicating with said passage, and a reference electrode is formed on the bottom of said groove.

10. An FET sensor apparatus of flow-cell adaptive type, comprising:

a sensor comprising a plurality of field-effect transistors hexagonal in shape with two elongate opposed sides formed on a semiconductor substrate, the semiconductor substrate having two major surfaces and a predetermined crystal plane, and each of the plurality of hexagonally-shaped field-effect transistors having at least a gate portion arranged on one of the major surfaces;

a base member having a plurality of through holes in which said hexagonally-shaped field-effect transistors are fitted, respectively; and support means for supporting said hexagonally-shaped field-effect transistors in said through holes in watertight fashion, with said gate portions exposed through an end of said through hole;

wherein said through hole of said base member has a shape complementary to that of said sensor; and wherein said through hole of said base member has a tapered surface, and said sensor is exposed through the opening of said through hole having a smaller diameter.

11. The FET sensor apparatus according to claim 10, wherein said field-effect transistors are electrically isolated from one another, by means of pn-junction isolation.

12. The FET sensor apparatus according to claim 10, wherein said base member is made of a semiconductor substrate of the same type of said semiconductor substrate on which said field-effect transistors are formed.

13. The FET sensor apparatus according to claim 12, wherein said semiconductor substrate forming said base member has an insulation film which covers at least those portions which have said through holes.

14. A method of manufacturing an FET sensor apparatus of flow-cell adaptive type, said method comprising the steps of:

etching one major surface of a semiconductor substrate in a semiconductor-manufacturing process, thereby forming a bottomed hole in the major surface, which has a predetermined diameter and a predetermined depth;

etching said semiconductor substrate, thereby forming a through hole in the bottom of said bottomed hole, which has a diameter less than that of said bottomed hole, thus forming a gate window; and inserting a sensor into, and fixing the same in, the gate window of said semiconductor substrate, said sensor comprising a semiconductor substrate having the same crystal plane as the semiconductor substrate.

15. The method according to claim 14, further comprising the step of forming an insulation film on at least those portions which have said through holes, after said gate window has been formed.

16. A flow-cell adaptive type FET sensor apparatus, comprising:

a sensor comprising a field-effect transistor hexagonal in shape with two elongate opposed sides formed on a first semiconductor substrate having a predetermined crystal face, a gate portion of said field-effect transistor being arranged on at least one of the side surfaces of said semiconductor substrate;

a base member having a through hole, in which the sensor is fitted, formed by processing a second semiconductor substrate having a predetermined crystal face by use of an anisotropic etching operation; and support means for adhesively supporting said sensor in the through hole of said base member with said gate portion being exposed through an opening of said through hole when said sensor is inserted into said through hole of said base member.

* * * * *